US00PP23267P2

(12) United States Plant Patent
de Wet et al.

(10) Patent No.: US PP23,267 P2
(45) Date of Patent: Dec. 18, 2012

(54) ***ALOE* PLANT NAMED 'X5'**

(50) Latin Name: ***Aloe* hybrid**
Varietal Denomination: X5

(76) Inventors: Charles Andrew de Wet, Johannesburg (ZA); Quinton Bean, Johannesburg (ZA)

( * ) Notice: Subject to any disclaimer, the term of this patent is extended or adjusted under 35 U.S.C. 154(b) by 122 days.

(21) Appl. No.: 13/065,628

(22) Filed: Mar. 25, 2011

(51) Int. Cl.
*A01H 5/00* (2006.01)

(52) U.S. Cl. ..... Plt./373; Plt./263.1

(58) Field of Classification Search ..... Plt./373, Plt./263.1, 258
See application file for complete search history.

*Primary Examiner* — June Hwu
(74) *Attorney, Agent, or Firm* — Penny J. Aguirre

(57) ABSTRACT

A new cultivar of *Aloe*, 'X5', characterized by its vigorous growth habit, its short and compact plant habit, its abundance of inflorescences on strong erect scapes, and its flowers that are greenish white in color and emerge from red-orange flower buds, which gives the inflorescence a strong bicolor appearance.

2 Drawing Sheets

Botanical classification: *Aloe* hybrid.
Varietal denomination: 'X5'.

BACKGROUND OF THE INVENTION

The present invention relates to a new and distinct cultivar of *Aloe* of hybrid origin, botanically known as *Aloe* 'X5' and will be referred to hereafter by its cultivar name, 'X5'. 'X5' is a new cultivar of flowering *Aloe* grown for landscape and container use.

The new cultivar was derived from a controlled breeding program establish by the Inventor at his nursery in Linbro Park, Republic of South Africa in 1973. The overall purpose of the breeding program is to make selections of hybrid *Aloe* with desirable horticultural characteristics to include improved vigor, flowering ability, and disease resistance. 'X5' was selected in the Inventor's trial bed in June 2006 as a single unique plant from amongst the seedlings derived from a cross made in 2005 between unnamed complex hybrids in the Inventor's breeding program as the female parent and male parents.

Asexual reproduction of the new cultivar was first accomplished by offshoots by the Inventor in Linbro Park, Republic of South Africa in 2006. The characteristics of this cultivar have been determined both by offshoots and in vitro propagation to be stable and to reproduce true to type in successive generations.

SUMMARY OF THE INVENTION

The following traits have been repeatedly observed and represent the characteristics of the new cultivar of *Aloe*. These attributes in combination distinguish 'X5' from all other selections of *Aloe* known to the Inventor.

1. 'X5' exhibits a vigorous growth rate.
2. 'X5' exhibits a short and compact plant habit.
3. 'X5' produces an abundance of inflorescences on strong erect scapes.
4. 'X5' exhibits flowers that are greenish white in color and emerge from red-orange flower buds forming a bicolored inflorescence.

'X5' can be distinguished from its parent plants. 'X5' differs from its female parent, in having a faster growth rate and in producing more inflorescences. 'X5' differs from its male parent in having a shorter and more compact plant habit and in producing flowers that are more intense in color. 'X5' can be most closely compared to another complex hybrid from the Inventor's breeding program, *Aloe* 'ANDHOGP' (not patented). 'X5' differs from 'ANDHOGP' in having straighter and narrower leaves with less distinct margins and in having red-orange to greenish white flowers on a bicolored inflorescence rather than a mono colored inflorescence with dull reddish pink flowers.

BRIEF DESCRIPTION OF THE DRAWING

The accompanying colored photographs illustrate the overall appearance and distinct characteristics of the new *Aloe*. The photographs were taken of a 2 year-old plant as grown outdoors in 3-liter containers in North West Province, Republic of South Africa.

The photograph in FIG. 1 illustrates the overall habit and appearance of 'X5' in bloom.

Figure 1:
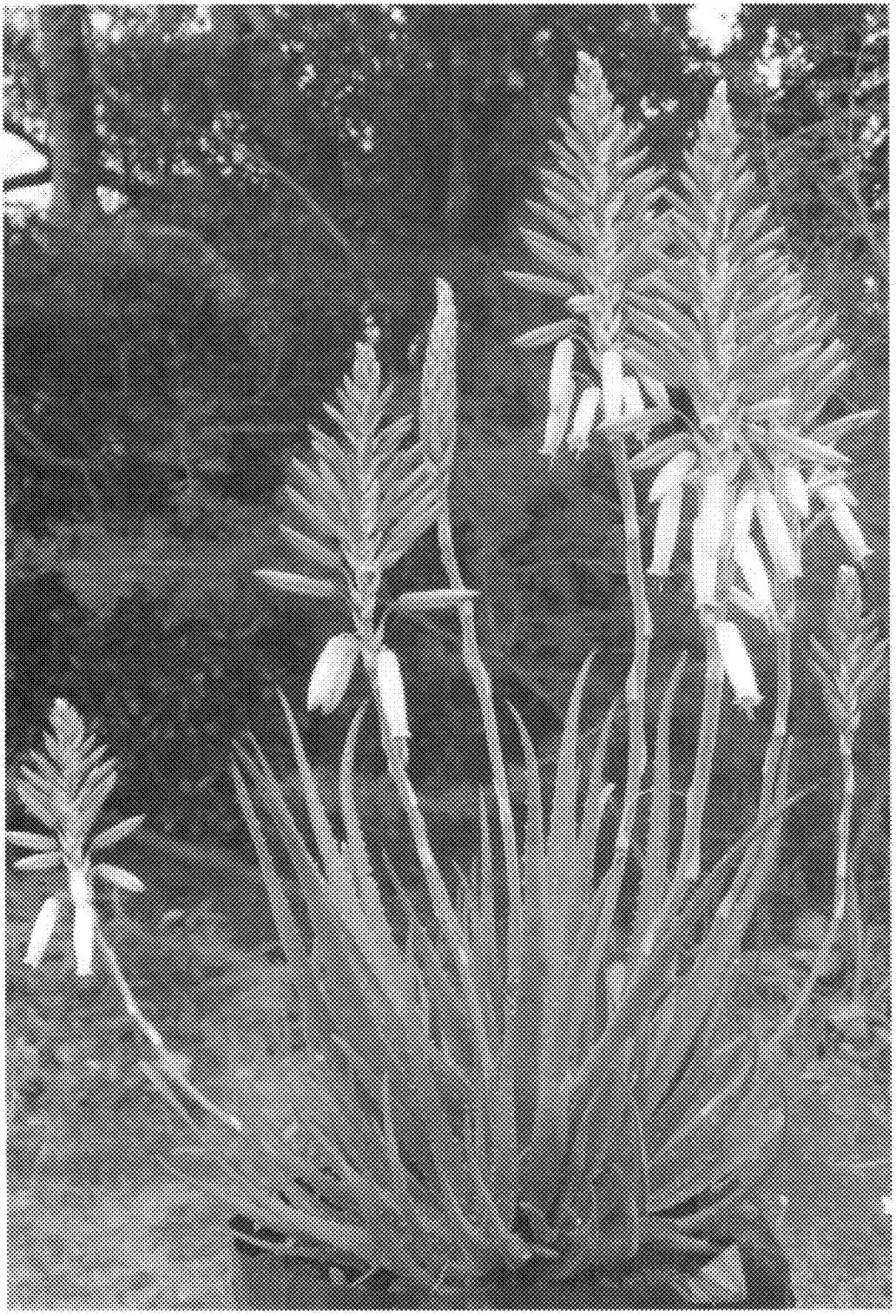
Figure 2:
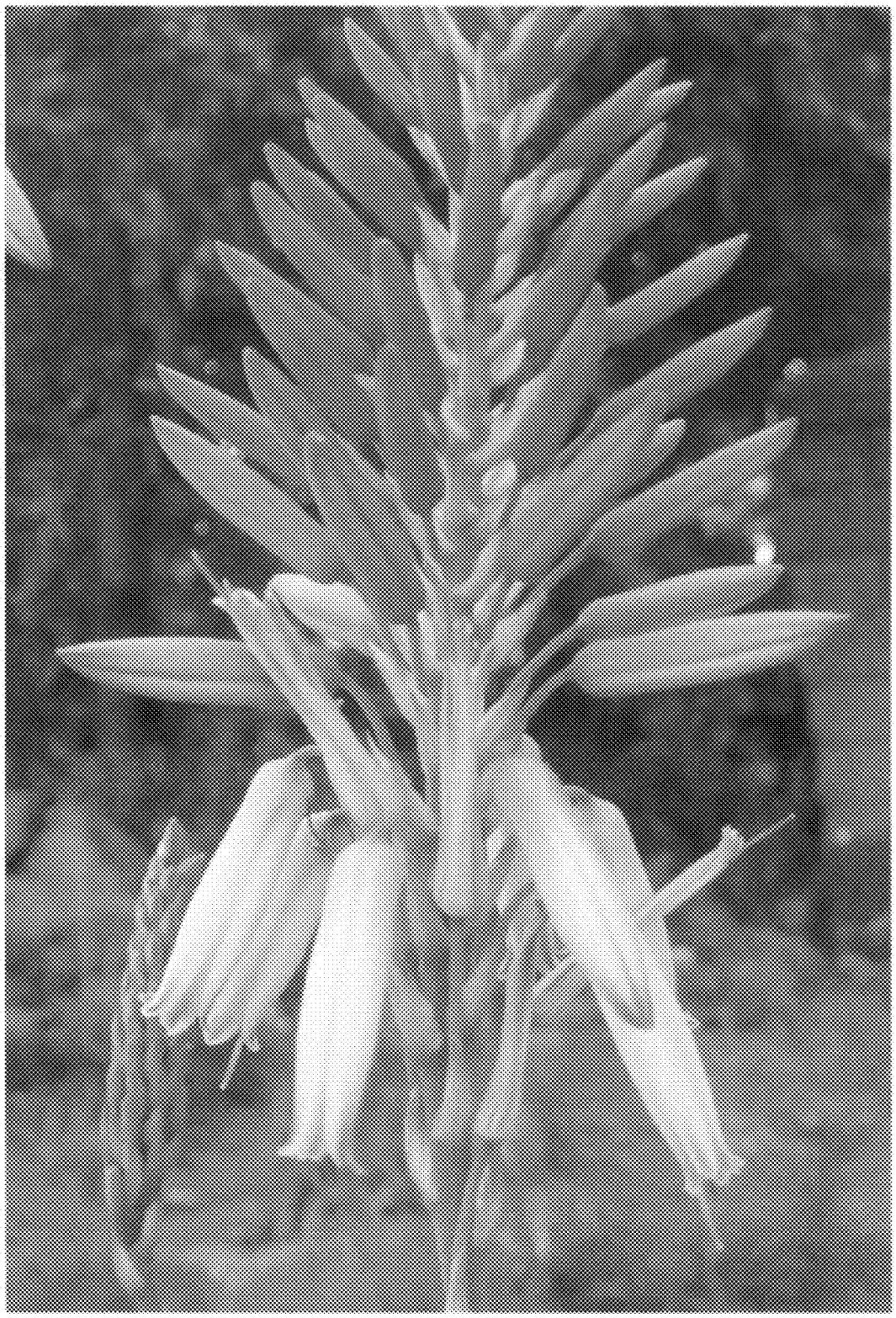

The photograph in FIG. 2 provides a close-up view of an inflorescence of 'X5'. The colors in the photograph may differ slightly from the color values cited in the detailed botanical description, which accurately describe the colors of the new *Aloe*.

DETAILED BOTANICAL DESCRIPTION

The detailed botanical data describes two-year old plants of 'X5' as grown in three-liter containers outdoors in North West Province, Republic of South Africa. The phenotype of the new cultivar may vary with variations in environmental, climatic, and cultural conditions, as it has not been tested under all possible environmental conditions. The color determinations are in accordance with The 2001 R.H.S. Colour Chart of The Royal Horticultural Society, London, England, except where general color terms of ordinary dictionary significance are used.

General description:

*Blooming habit*.—Blooms autumn through winter to spring and erratically throughout the year.

*Plant type*.—*Aloe* hybrid, monoecious, evergreen.

*Plant habit*.—Clump forming, rosulate leaf succulent.

*Height and spread*.—About 30 cm in height and 30 cm in width.

*Hardiness*.—U.S.D.A. Zone 10a.

*Diseases and pests*.—No unique aspects concerning susceptibility or resistance.

*Growing conditions*.—Tolerant in a range of soils from humic to sandy to light clay, performs well in full to filtered sun.

*Root description*.—Superficial network of soft roots.

Growth and propagation:

*Propagation*.—Offshoots or tissue culture.

*Time required for root development*.—Between 7 to 21 days at an average air temperature of 15° C. to 25° C.

*Time required to develop flowering sized plants*.—9 to 12 months.

*Growth rate*.—Very vigorous.

Stem description:

*Branching habit*.—From base.

*Stem angle*.—45° to 60° angle to the soil line.

*Stem surface*.—Glabrous.

*Internode length*.—2 to 3 mm.

*Stem color*.—189B.

Foliage description:

*Leaf shape*.—Narrowly sword-shaped, elongated.

*Leaf division*.—Simple.

*Leaf base*.—Clasping to stem.

*Leaf apex*.—Tapering to a sharp point.

*Leaf aspect*.—Sulcate.

*Leaf venation*.—Indistinct longitudinal lines.

*Leaf margins*.—Adorned with short evenly spaced white marginal teeth.

*Leaf arrangement*.—Rosulate, around a central axis.

*Leaf attachment*.—Sessile.

*Leaf size*.—Average of 12 to 2.2 cm in width and an average of 20 to 25 cm in length.

*Leaf number*.—Average of 80 as grown in a 3-liter container.

*Leaf surface*.—Glabrous and slightly glaucous with teethed margins.

*Leaf color*.—Upper and lower surface; 189A.

Flower description:

*Inflorescence type*.—Dense racemes of single flowers held on erect and strong scapes.

*Inflorescence size*.—From 20 cm to 25 cm in length and an average of 10 cm in width.

*Flower fragrance*.—None.

*Flower quantity*.—An average of 20 to 40 flowers per inflorescence, an average of 6 inflorescences as grown in a 3-liter container.

*Flower lastingness*.—Flowers open from base towards the apex, average of 5 days per flower, not persistent.

*Flower buds*.—Tubular, closed at tip, between 2 to 6 mm in diameter and 5 to 25 mm in length, 180B in color with very apex about 201C.

*Flower aspect*.—Drooping.

*Flower shape*.—Tubular.

*Flower size*.—An average of 2.9 cm in length and 6 mm in diameter.

*Tepals*.—6, 2.6 to 3.2 cm in length, about 6 mm in diameter, fused into tube with triangular-shaped free apex (about 2 mm in length and width), margin is entire, apex broadly acute, upper and lower surface is glabrous and smooth, color when fully open on outer and inner surface 157B and lightly suffused with 138C.

*Peduncles* (*scapes*).—About 20 to 25 cm in length and an average of 6 to 8 mm in diameter, held erect, very strong, color is 189B, surface is glabrous and slightly glaucous.

*Peduncle bracts*.—1 cm in length and 7 mm in width, ovate shape, glabrous on both surfaces, truncate base, apiculate apex, 158B slightly fused with 180C in color.

*Pedicels*.—Average of 1.8 to 2 cm in length and 1 mm in diameter, 138A and 138B in color on mature flowers, glabrous surface.

Reproductive organs:

*Gynoecium*.—1 pistil, stigma is capitate, minute; about 0.25 mm and 160A in color, style is thread-like; about 2.2 cm in length and 160A in color, ovary is superior, cylindrical in shape, about 5 mm in length and 2 mm in width and 189A in color.

*Androcoecium*.—6 stamens inserted at base of ovary, anthers are about 2 mm in length and 1 mm width and 175A color, filaments are about 2.2 cm in length and 1 mm in width, at about 160A in color, pollen is low in quantity and 162B in color.

*Seed*.—Few seeds produced, irregularly angled with a short wing, about 3 mm in length and 1 mm in width, 201A in color.

It is claimed:

1. A new and distinct cultivar of *Aloe* plant named 'X5' as herein illustrated and described.

* * * * *